United States Patent

Weisse et al.

Patent Number: 5,329,049
Date of Patent: Jul. 12, 1994

[54] PROCESS FOR THE PREPARATION OF SUBSTITUTED INDANONES

[75] Inventors: Laurent Weisse, Oberursel; Heinz Strutz, Usingen, both of Fed. Rep. of Germany

[73] Assignee: Hoechst Aktiengesellschaft, Frankfurt am Main, Fed. Rep. of Germany

[21] Appl. No.: 53,716

[22] Filed: Apr. 27, 1993

[30] Foreign Application Priority Data

Apr. 28, 1992 [DE] Fed. Rep. of Germany ....... 4213939

[51] Int. Cl.$^5$ .............................................. C07C 45/45
[52] U.S. Cl. ................................... 568/319; 568/327
[58] Field of Search ................................ 568/319, 327

[56] References Cited

U.S. PATENT DOCUMENTS

| | | | |
|---|---|---|---|
| 1,754,031 | 4/1930 | Mayer et al. | 568/319 |
| 3,324,174 | 6/1967 | Braun et al. | 568/319 |
| 3,950,408 | 4/1976 | Chamberlin et al. | 568/327 |
| 3,970,693 | 7/1976 | Tull et al. | 568/327 |
| 4,541,948 | 9/1985 | Joulain | 568/326 |
| 4,568,782 | 2/1986 | Pagnotta et al. | 568/327 |

FOREIGN PATENT DOCUMENTS

| | | |
|---|---|---|
| 0203276 | 12/1986 | European Pat. Off. |
| 3519009 | 11/1986 | Fed. Rep. of Germany |
| 51-065742 | 4/1976 | Japan |

OTHER PUBLICATIONS

Olah, G. A., Ed., *Friedel-Crafts and Related Reactions;* vol. I, Interscience, N.Y., 1963, pp. 318-321.
Journal of the American Chemical Society, vol. 72, 1950, pp. 3286 and 3287.
Fieser et al, J.A.C.S., vol. 61, pp. 1272-1281 (1939).
Sethna, "Friedel-Crafts & Related Reactions", pp. 911-921 (1964).
Marquardt, Helv. Chim. Acta, vol. 48, pp. 1476-1485 (1965).

*Primary Examiner*—James H. Reamer

[57] ABSTRACT

1-Indanones of the formula III or IIIa

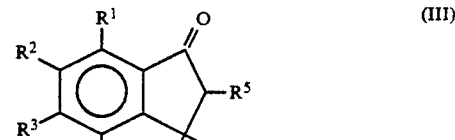

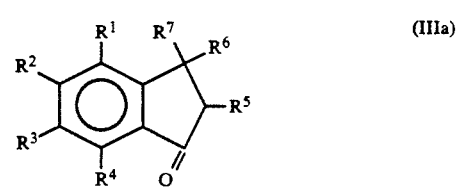

in which $R^1$ to $R^7$ are preferably hydrogen or alkyl, or adjacent radicals $R^1$ to $R^4$ form a ring, are obtained in a one-step reaction by reacting a compound I

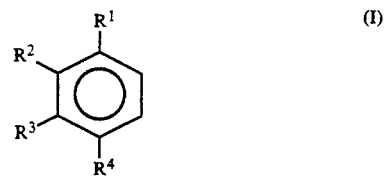

with a compound of the formula II

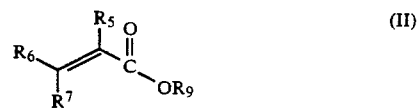

in liquid hydrogen fluoride.

5 Claims, No Drawings

PROCESS FOR THE PREPARATION OF SUBSTITUTED INDANONES

DESCRIPTION

The present invention relates to a technically simple process for the preparation of substituted 1-indanones.

Compounds of this type are important intermediates in the preparation of metallocene complexes, since 1-indanones can readily be converted into the corresponding indenes. Indenes are used as a ligand system for the synthesis of metallocene complexes (EP-A 336 128). In particular the corresponding bridged, chiral zirconium derivatives are of considerable importance as highly active catalysts in the polymerization of olefins (cf. EP-A 129 368 and EP-A 321 852). By varying the ligand system, for example by substitution, the catalyst properties can be modified in a targeted manner. This makes it possible to change the polymer yields, the molecular weight, the tacticity or the melting point of the polymers to the desired extent (New J. Chem. 14 (1990) 499; Organomet. 9 (1990) 3098; Angew. Chem. 102 (1990) 339; EP-A 316 155; EP-A 351 392).

Furthermore, substituted 1-indanones are of industrial importance as fragrances (EP-A 162 465) and as valuable intermediates in the preparation of pharmaceutical products or other bioactive compounds (EP-A 421 759; J. Med. Chem. 25 (1990) 765).

The literature describes a number of processes for the preparation of substituted 1-indanones.

1-Indanones which carry substituents on the 6-membered ring can be prepared starting from the correspondingly substituted aromatic compounds by fusing on the 5-membered ring in 2- to 6-step syntheses (J. Org. Chem., 55 (1990) 247; Bull. Soc. Chim. Fr. 6 (1969) 1981).

Processes for the preparation of 1-indanones which carry substituents on the 5-membered ring or on both rings are likewise known (J. Org. Chem. 46 (1981) 3758; J. Org. Chem. 23 (1958) 1441).

These methods have the disadvantage that they are generally multistep and give only poor overall yields of the desired products. Many of the syntheses are not universally applicable, but are restricted to specific derivatives. In others, the starting materials are poorly accessible or very expensive. Certain substitution patterns on the aromatic ring can likewise not be achieved by these methods. The few known one-step syntheses have the disadvantage that they are restricted to specific derivatives and give poor yields, so that technically complex purification operations on the products are necessary. Most of these reactions are carried out with the aid of Friedel-Crafts catalysts, such as, for example, $AlCl_3$, which are employed in excess. These reactions require technically complex work-up steps, which are associated with production of a large amount of salt.

Also known are processes for the preparation of substituted indanones by reacting aromatic compounds, such as xylene or acenaphthene, with aqueous methacrylic acid, crotonic acid or cinnamic acid in a large excess of liquid hydrogen fluoride (J. Am. Chem. Soc. 61 (1939) 1272; J. Am. Chem. Soc. 72 (1950) 3287). The yields are between 62% and 81%. This method has the disadvantage that water present or formed causes considerable corrosion problems. Recycling of the hydrogen fluoride is likewise not possible due to the presence of water. The hydrofluoric acid must be neutralized, producing a large amount of salt which is difficult to dispose of. In addition, the products must also be purified due to the low yields.

The object was thus to find a process for the preparation of the abovementioned indanones which avoids the disadvantages known from the prior art.

Completely surprisingly, it has been found that aromatic compounds of the formula I below react virtually quantitatively with commercial carboxylic esters of the formula II in liquid hydrogen fluoride to give indanones of the formula III/IIIa. Complex cleaning of the products is therefore unnecessary. In addition, this process is a one-step process which is simple to perform industrially. Since the alcohols formed do not dehydrate under the reaction conditions, hydrofluoric acid, which is prohibitive in an industrial process, is not formed. This method is thus an economically favorable and novel process for the preparation of substituted 1-indanones. At the same time, the process enables the preparation of novel compounds of said structural type.

The present invention therefore relates to a process for the preparation of a compound of the formula III or the isomer thereof of the formula IIIa

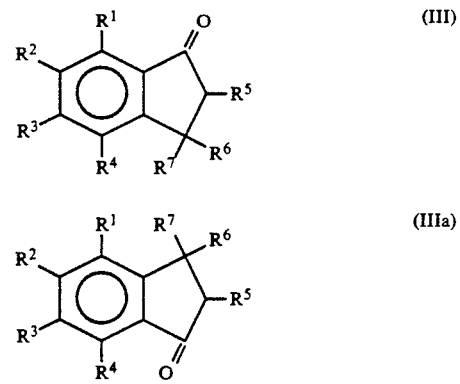

in which $R^1$, $R^2$, $R^3$, $R^4$, $R^5$, $R^6$ and $R^7$ are identical or different and are hydrogen, $(C_1-C_{20})$-alkyl, $(C_6-C_{14})$-aryl, $(C_1-C_{10})$alkoxy, $(C_2-C_{10})$alkenyl, $(C_7-C_{20})$arylalkyl, $(C_7-C_{20})$alkylaryl, $(C_6-C_{10})$aryloxy, $(C_1-C_{10})$-fluoroalkyl, $(C_6-C_{10})$haloaryl, $(C_2-C_{10})$alkynyl, an $-SiR^8_3$ radical in which $R^8$ is $(C_1-C_{10})$alkyl, or are a halogen atom or a heteroaromatic radical having 5 or 6 ring members which may contain one or more heteroatoms, or the adjacent radicals $R^1-R^4$, together with the atoms connecting them, form one or more substituted or unsubstituted rings, which comprises reacting a compound of the formula I

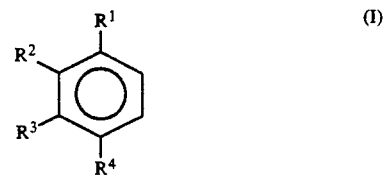

with a compound of the formula II

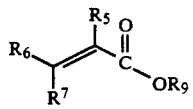

(II)

in which $R^9$ is straight-chain $(C_1-C_{20})$alkyl, and the substituents $R^1-R^7$ are as defined above, in liquid, anhydrous hydrogen fluoride.

Alkyl here is straight-chain or branched alkyl. Halogen is fluorine, chlorine, bromine or iodine, in particular fluorine or chlorine. Examples of heteroaromatic radicals are thienyl, furyl or pyridyl.

The rings formed by adjacent radicals $R^1-R^4$ may be substituted by substituents as defined for $R^1-R^7$, including the preferred meanings mentioned therefor.

In the formulae III and IIIa, $R^1$, $R^2$, $R^3$ and $R^4$ are preferably identical or different and are hydrogen, $(C_1-C_{10})$alkyl, $(C_1-C_4)$alkoxy, $(C_2-C_6)$alkenyl, $(C_1-C_6)$fluoroalkyl or a halogen atom, or the radicals $R^1$ and $R^2$, $R^2$ and $R^3$ or $R^3$ and $R^4$, together with the atoms connecting them, form a substituted or unsubstituted five- or six-membered ring, and $R^5$, $R^6$ and $R^7$ are hydrogen or $(C_1-C_{10})$alkyl.

In particular, $R^1$, $R^2$, $R^3$ and $R^4$ are identical or different and are hydrogen or $(C_1-C_{10})$alkyl, or the radicals $R^1$ and $R^2$, $R^2$ and $R^3$ or $R^3$ and $R^4$, together with the atoms connecting them, form a substituted or unsubstituted, five- or six-membered, saturated or unsaturated carbocyclic ring, and $R^5$, $R^6$ and $R^7$ are identical or different and are hydrogen or methyl.

The saturated or unsaturated five- or six-membered ring carbocyclic ring) formed by adjacent substituents $R^1-R^4$ may carry additional substituents, preferably $(C_1-C_{10})$alkyl.

Depending on the substitution pattern on the aromatic ring, the indanones may be formed in the form of two constitutional isomers of the formulae III and IIIa. Depending on the application, these may be further reacted in pure form or as a mixture. In the preparation of metallocene complexes or if the 1-indanes are used as fragrances, the isomer mixture can be employed.

The indanones III/IIIa are preferably prepared by reacting aromatic compounds of the formula I with esters of the formula II.

The starting compounds are commercially available or can be prepared by methods known from the literature.

In the preparation of the compounds III/IIIa, additional solvent can be added to the hydrogen fluoride, but the reaction is preferably carried out in pure, anhydrous hydrogen fluoride.

The molar ratios between the starting compounds, including the hydrogen fluoride, can vary within broad limits. The molar ratio of compound I:II:HF is preferably 1:0.5-2.0:5-100, in particular 1:0.9-1.2:20-50, i.e. the reaction is carried out in an excess of hydrogen fluoride.

The reaction temperature is preferably from −30° C. to 130° C. in particular from 0° C. to 80° C.

The reaction times generally vary between 30 minutes and 50 hours, preferably between 1 hour and 24 hours.

The reaction is preferably carried out in a pressure range of 1-15 atm.

It is preferred to initially introduce a mixture of the compounds I and II and to meter in the hydrogen fluoride. The reverse sequence of addition is also possible.

When the reaction is complete, the hydrogen fluoride can be removed by distillation and recovered virtually quantitatively without significant impurities. The residue can then be freed from the alcohol formed or traces of hydrogen fluoride by distillation.

The indanones of the formulae III and IIIa can be freed from acid components by washing with $Na_2CO_3$, $NaHCO_3$ or KOH solution and water and dried using conventional dessicants, such as $Na_2SO_4$, $MgSO_4$ or molecular sieves. Since the reactions are generally virtually quantitative, further purification is in most cases unnecessary. However, filtration through silica gel, aluminum oxide or filtration aids, such as, for example, Celite, is frequently advisable. If necessary, the further purification can be carried out by distillation, column chromatography or crystallization. If necessary, the constitutional isomers III and IIIa can be separated from one another by column chromatography on silica gel or aluminum oxide.

The process according to the invention is distinguished, in particular, by the fact that variously substituted 1-indanones can be obtained very selectively and in virtually quantitative yield in a simple and short synthesis (one-step process). Complex purification of the derivatives is therefore unnecessary, in contrast to the prior art. A further advantage is that the hydrogen fluoride used as catalyst can be recovered virtually quantitatively and re-used, since no water is formed during the reaction. This has the further, industrially crucial advantage that corrosion problems caused by aqueous hydrofluoric acid are avoided. This method thus represents an economically and ecologically very favorable process for the preparation of substituted 1-indanones. The substitution pattern on the five- and six-membered rings can be varied in a very broad range, also allowing access to novel 1-indanone derivatives.

The indanones III/IIIa are preferably used for the preparation of metallocenes (cf., for example, EP-A 336 128) or as fragrances (EP-A 162 465). To prepare the metallocenes, the indanones, preferably as an isomer mixture, are first reduced to the corresponding indanols by methods known from the literature using reducing agents such as $NaBH_4$ or $LiAlH_4$, and these are subsequently dehydrated to give the corresponding indenes using acids such as sulfuric acid, oxalic acid or p-toluenesulfonic acid or alternatively by treatment with dehydrating substances such as magnesium sulfate, sodium sulfate, aluminum oxide, silica gel or molecular sieves (Bull. Soc. Chim. Fr. 11 (1973) 3092; Organomet. 9 (1990) 3098).

The substituted indenes may be obtained as double-bond isomers. These can be purified from byproducts by distillation, column chromatography or crystallization. The isomers can be employed, as a mixture, directly for the synthesis of the corresponding metallocene complexes.

The synthesis of the metallocenes starting from indenes is known (AU-A-31478/89; J. Organomet. Chem. 342 (1988) 21; EP-A 284 707).

The examples below serve to illustrate the invention in greater detail.

EXAMPLE A 3,3,4,6-Tetramethyl-1-indanone ( 1 ) and 3,3,5,7-tetramethyl-1-indanone (1a)

100 g (5 mol) of anhydrous hydrogen fluoride were added to 10.6 g (100 mmol) of m-xylene (99%) and 14.4 g (112 mmol) of ethyl 3,3-dimethylacrylate in a 250 ml stainless steel autoclave, and the mixture was stirred at 50° C. for 18 hours. Hydrogen fluoride was then removed by distillation, and the residue was taken up in ethyl acetate and neutralized by means of dilute KOH solution. The aqueous phase was separated off and extracted twice with ethyl acetate. The combined organic phases were dried using MgSO$_4$ and freed from solvent under reduced pressure, giving 18.5 g of a pale brown oil. The selectivities to (1) and (1a) were 78% and 21% respectively. (Yield: 76% and 20.7% of theory, respectively).

$^1$H-NMR spectra (100 MHz, CDCl$_3$): 1:7.36 (d,1H), 7.18 (d,1H), 2.57 (s,2H), 2.47 (s,3H), 2.32 (s,3H), 1.47 (s,6H); 1a: 7.07 (d, 1H), 6.9 (d, 1H), 2.6–2.3 (m,8H), 1.37 (s,6H)

EXAMPLE B

3,3,4,7-Tetramethyl-1-indanone (2)

10.6 g (100 mmol) of p-xylene (99% purity) and 14.4 g (112 mmol) of ethyl 3,3-dimethylacrylate were reacted with liquid fluoride and worked up analogously to Example A, giving 18 g of the compound (2) in a purity of 96% (GC). (Yield: 92% of theory).

$^1$H-NMR spectra (100 MHz, CDCl$_3$): 2:7–17 (d, 1H), 6.99 (d, 1H), 2.57 (s,2H), 2.55 (s,3H), 2.45 (s,3H), 1.47 (s,3H)

EXAMPLE C

3,3-Dimethyl-1-indanone (3)

7.81 g (100 mmol) of benzene and 14.4 g (112 mmol) of ethyl 3,3-dimethylacrylate were reacted analogously with 100 g (5 mol) of liquid hydrogen fluoride and the mixture was stirred at 70° C. for 1 hour. The work-up was carried out analogously to Example A, giving 15.5 g of the compound (3) in a purity of 96% (GC). (Yield: 93.1% of theory). $^1$H-NMR spectra (100 MHz, CDCl$_3$): 3:7.77–7.25 (m,4H), 2.57 (s,2H), 1.37 (s,6H).

EXAMPLE D

4,7-Dimethyl-3-phenyl-1-indanone (4)

100 g (5 mol) of anhydrous hydrogen fluoride were added to 10.6 g (100 mmol) of p-xylene (99% purity) and 17 g (105 mmol) of methyl trans-cinnamate, and the mixture was stirred at 70° C. for 17 hours. Work-up carried out analogously to Example A gave 23.6 g of a yellowish solid. The purity of the product is 96% (GC). (96% of theory). After recrystallization once from an ethyl acetate/hexane mixture (1:1), a virtually white solid was obtained in a yield of 90%. The purity after this step is greater than 98% (GC).

$^1$H-NMR spectra (300 MHz, CDCl$_3$):4:7.27–6.97 (m,7H), 4.48 (dd, 1H), 3.16 (dd, 1H), 2.66 (s,3H), 2.54 (dd, 1H), 1.95 (s,3H).

EXAMPLE E

3,4,7-Trimethyl-1-indanone (5)

100 g (5 mol) of hydrogen fluoride were added to 10.6 g (100 mmol ) of p-xylene and 12.5 g (109 mmol ) of ethyl crotonate, and the mixture was stirred at 70° C. for 20 hours. Work-up carried out analogously to Example A gave 12 g of the compound (5) in a purity of 80% (GC). (Yield: 55% of theory).

We claim:

1. A process for the preparation of a compound of the formula III or the isomer thereof of the formula IIIa

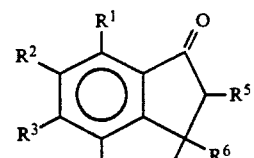

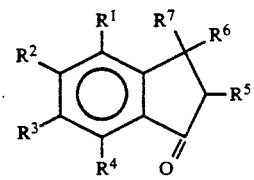

in which
R$^1$, R$^2$, R$^3$, R$^4$, R$^5$, R$^6$ and R$^7$ are identical or different and are hydrogen, (C$_1$–C$_{20}$ )-alkyl, (C$_6$–C$_{14}$)aryl, (C$_1$–C$_{10}$)alkoxy, (C$_2$–C$_{10}$)alkenyl, (C$_7$–C$_{20}$)arylalkyl, (C$_7$–C$_{20}$)alkylaryl, (C$_6$–C$_{10}$)aryloxy, (C$_1$–C$_{10}$)-fluoroalkyl, (C$_6$–C$_{10}$)haloaryl, (C$_2$–C$_{10}$)alkynyl, an —SiR$^8$$_3$ radical in which R$^8$ is (C$_1$–C$_{10}$)alkyl, or are a halogen atom or a heteroaromatic radical having 5 or 6 ring members which may contain one or more heteroatoms, or the adjacent radicals R$^1$, R$^2$, R$^3$ and R$^4$, together with the atoms connecting them, form one or more substituted or unsubstituted rings, which comprises reacting a compound of the formula I

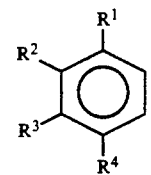

with a compound of the formula II

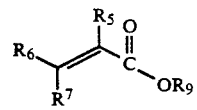

in which R$^9$ is straight-chain (C$_1$–C$_{20}$)alkyl, and R$^1$ to R$^7$ are as defined above, in liquid, anhydrous hydrogen fluoride.

2. The process as claimed in claim 1, wherein, in the formulae III and IIIa, are identical R$^1$, R$^2$, R$^3$ and R$^4$ are identical or different and are hydrogen, (C$_1$–C$_{10}$)alkyl, (C$_1$–C$_4$)alkoxy, (C$_2$–C$_6$)alkenyl, (C$_1$–C$_6$)fluoroalkyl or a halogen atom, or the radicals R$^1$ and R$^2$, R$^2$ and R$^3$ or R$^3$ and R$^4$, together with the atoms connecting them, form a substituted or unsubstituted, five- or six-membered ring, and R$^5$, R$^6$ and R$^7$ are hydrogen or (C$_1$–C$_{10}$)alkyl.

3. The process as claimed in claim 1, wherein, in the formulae III and IIIa, R$^1$, R$^2$, R$^3$ and R$^4$ are identical or different and are hydrogen or (C$_1$–C$_{10}$)alkyl, or the radicals R$^1$ and R$^2$, R$^2$ and R$^3$ or R$^3$ and R$^4$, together with the atoms connecting them, form a substituted or unsubstituted, six-membered, saturated or unsaturated carbocyclic ring, and R$^5$, and R$^6$ and R$^7$ are identical or different and are hydrogen or methyl.

4. The process as claimed in claim 1, wherein the molar ratio between compound I: compound II: hydrogen fluoride is 1:0.5–2.0:5–100.

5. The process as claimed in claim 1, wherein a compound of the formula I is reacted with a compound of the formula II.

* * * * *